US006355455B1

(12) United States Patent
Pauly et al.

(10) Patent No.: US 6,355,455 B1
(45) Date of Patent: Mar. 12, 2002

(54) METHOD FOR ENZYMATIC SYNTHESIS OF SUCROSE ESTERS

(75) Inventors: Gilles Pauly, Nancy; Jean-Marc Engasser, Ludres; Mohammed Ghoul, Nancy, all of (FR)

(73) Assignee: Laboratoires Serobiologiques (Societe Anonyme), Pulnoy (FR)

( * ) Notice: Subject to any disclaimer, the term of this patent is extended or adjusted under 35 U.S.C. 154(b) by 0 days.

(21) Appl. No.: 09/462,427

(22) PCT Filed: Jul. 8, 1998

(86) PCT No.: PCT/FR98/01479

§ 371 Date: Jan. 10, 2000

§ 102(e) Date: Jan. 10, 2000

(87) PCT Pub. No.: WO99/02722

PCT Pub. Date: Jan. 21, 1999

(30) Foreign Application Priority Data

Jul. 9, 1997 (FR) .............................................. 97 08916

(51) Int. Cl.$^7$ .............................. C12P 7/62; C12P 19/12; C12N 9/20; C12N 9/50
(52) U.S. Cl. ........................ 435/135; 435/100; 435/198; 435/219; 536/115; 536/119
(58) Field of Search .................................. 435/135, 100, 435/198, 219; 536/115, 119

(56) References Cited

FOREIGN PATENT DOCUMENTS

| EP | 0 087 404 | 8/1983 |
| EP | 0 413 307 | 2/1991 |
| EP | 0 507 323 | 10/1992 |
| JP | 05 317064 | 12/1993 |
| JP | 09 154595 | 6/1997 |
| JP | 09 173091 | 7/1997 |

*Primary Examiner*—Francisco Prats
*Assistant Examiner*—Susan D. Coe
(74) *Attorney, Agent, or Firm*—Young & Thompson

(57) ABSTRACT

A method for the enzymatic synthesis of sucrose ester, comprises introducing, in an adapted reactor and so as to form a reaction medium, predetermined amounts of an organic solvent, a sugar or a sugar derivative, a compound donor of acyl groups and an enzymatic catalyst, the amount of at least one constituent of the reaction mixture being deficient, in controlled addition during the reaction of additional amounts of the deficient constituent(s), and finally purifying the resulting sucrose esters at least by separating the fine enzymatic particles from the solvent.

13 Claims, No Drawings

METHOD FOR ENZYMATIC SYNTHESIS OF SUCROSE ESTERS

CROSS REFERENCE TO RELATED APPLICATION

This is the 35 USC 371 national stage of international application PCT/FR98/01479 filed Jul. 8, 1998, which designated the United States of America.

FIELD OF THE INVENTION

The invention concerns the field of processes for synthesising substances and relates to a method for enzymatic synthesis of sucrose esters.

BACKGROUND OF THE INVENTION

Sucrose esters are surfactants resulting from the combination of a sugar with a fatty acid by an ester bond. By varying the nature of the sugar and the length of the fatty chain it is possible to obtain a group of molecules which have a very wide range of hydrophilic-lipophilic balances and thus of functional properties. One can thus produce foaming, non-foaming, liquefying, solubilising and emulsifying surfactants.

These products are natural ingredients relating to the cleaning, cosmetic, pharmaceutical and agro-nutrition sectors.

The sucrose esters which are now commercially available are generally produced by chemical synthesis.

They are generally complex mixtures of various compounds, as a result of the non-specific nature of the chemical condensation reactions between the sugars and fatty acids. The high temperatures and pressures necessary for these reactions thus also lead to parasitic reactions and colouring of the products.

Sucrose esters may also be obtained by condensation reactions catalysed by enzymes, for example lipases. These enzymatic reactions have the advantage of being more specific than chemical synthesis and taking place at normal temperatures and pressures.

SEINO et al. have proposed (J. Am Oil Chem. Soc. 61, 1761–1765, 1984) esterifying sugars (sucrose, glucose, fructose, sorbitol) with fatty acids (stearic, oleic, linoleic) in the presence of an enzyme in an aqueous medium. But this technology does not enable significant quantities of sucrose esters to be obtained.

Specifications WO 90/09451 and WO 94/01575 further describe methods of obtaining sucrose esters in the total absence of water and without using any solvent. However this technology necessitates preliminary alkylation of the sugars to allow them to be solubilised in the fatty phase. This technology for the production of esters from alkyl sugars and fatty acids also has the disadvantage of producing a preparation containing an excess of non-converted fat and thus of necessitating complex purifying operations if high purity levels are required for the resultant sucrose esters. Moreover the high viscosity of the reaction materials used makes the operations complicated to carry out.

ZAKS A. and KLIBANOV A. M. (Proc. Natl. Acad. Sci. USA, 82, 3192–3196, 1985) have firstly described enzymatic synthesis of sucrose esters of fatty acids in an organic solvent. However the pyridine used is a toxic solvent which is prohibited for industrial applications.

In addition, the use of organic solvents of the tertiary alcohol type to carry out enzymatic synthesis of sucrose esters has also already been proposed.

Thus specification FR-A-2 646 439 and KHALED et al. (Biotech. Letters, 13, 167–172, 1991) describe the synthesis of fructose, sorbose, sorbitol and mannitol oleate and fructose palmitate using an immobilised lipase and 2-methyl-2-butanol as solvent. However these synthesising processes still have a poor performance: final sucrose ester concentrations of the order of 20 g/l, sugar conversion yields of no more than 50% and specific productivity of below 0.01 g of sucrose esters produced per hour per gram of catalyst. Moreover the excessive amounts of fatty acids used necessitate complex operations to fractionate the mixtures of sucrose esters and fats obtained.

DUCRET et al (Biotechnol. Bioeng. 48, 214–221, 1995) describe the synthesis of fructose and glucose oleate in 2-methyl-2-butanol by an immobilised lipase, with a partial vacuum being maintained above the reaction medium. This technology gives higher degrees of conversion, 93% for fructose oleate and 70% for glucose oleate. However the final concentrations of sucrose esters are still low (23 g/l for fructose oleate, 17 g/l for glucose oleate) and the specific productivity is less than 0.1 g of sucrose ester per hour per gram of catalyst. Nor does the technology enable esters of saccharose or lactose to by synthesised.

Finally, WOUDENBERG et al. (Bioeng. 49, 328–333, 1996) describe enzymatic esterification of disaccharides such as sucrose with ethyl butanoate and ethyl dodecanoate, using an immobilised lipase and 2-methyl-2-butanol as solvent. But the final concentrations and specific productivity (0.04 g/h.g) obtained are very low.

SUMMARY OF THE INVENTION

The main aim of the invention is to alleviate all the foresaid disadvantages and to propose a method for enzymatic synthesis of sucrose esters which, compared to the known methods mentioned above, enables a clearly improved performance to be obtained in terms of final concentrations of sucrose esters, conversion yields (for both the sugars and fats originally present) and specific productivity, while reducing the complex, tedious post-synthesis purifying operations.

To this end the invention concerns a method for the enzymatic synthesis of sucrose esters, characterised in that it consists in introducing, in an adapted reactor and so as to form a reaction medium, predetermined amounts of an organic solvent, a sugar or a sugar derivative, a compound donor of acyl groups and an enzymatic catalyst, the amount of at least one constituent of the reaction mixture being deficient, in controlled addition during the reaction of additional amounts of the deficient constituent(s), and finally, in purifying the resulting sucrose esters at least by separating the enzymatic particles (for example by decanting, filtering or centrifuging) and the solvent (for example by evaporation, distilling or membrane filtration).

The method according to the invention more specifically consists, in the course of the synthesising reaction, of continuously or intermittently adding to the reaction medium defined additional quantities of sugar or sugar derivative in solid form or in the form of a liquid solution, of solvent, of enzymatic catalyst in soluble or immobilised form and/or of acyl-donor compound alone or solubilised in the solvent.

Thus the main difference between the method of the invention and the known methods previously described is the manner in which the enzymatic reaction is conducted.

In known methods for enzymatic synthesis of sucrose esters the full quantities of constituents of the reaction medium are placed in the reactor at the beginning of the reaction.

Now according to the invention only a defined initial quantity of one or more constituents of the reaction medium is initially placed in the reaction vessel, and additional quantities of the constituent or constituents partially introduced at the beginning are added in the course of the synthesising reaction.

By checking the quantity of reagents added it is possible to control how the composition of the reaction medium develops in the course of time, and thereby to direct the enzymatic reaction to maximum production of monoesters and/or diesters, while limiting parasitic reactions.

In accordance with the invention the reaction is conducted in such a way that the inhibition of the enzymatic reaction which is observed in the presence of strong concentrations of sugars or acyl donors is initially limited.

It has thus been found that, to obtain a high final concentration of sucrose esters, it is preferable not to place the full quantities of the necessary reagents in the reactor to begin with, but rather to introduce them gradually in a controlled manner in the course of the reaction, and to avoid reaching concentration levels which would inhibit the enzyme reaction.

The reaction is conducted in such a way that the molar ratio of [sugar(s) or sugar derivative(s)/acyl(s) donor] is controlled for its whole duration.

The molar ratio may advantageously be from 0.01 to 10.00, preferably from 0.02 to 2.00, according to the constituents forming the sugar(s) or sugar derivative(s)/acyl(s) donor pair in question.

By fixing molar ratio values within the above ranges in the reaction medium it is possible to obtain either higher reaction speeds or maximum proportions of sucrose monoesters or diesters.

By controlling the nature and quantity of the reagents added in the course of time one can either keep the molar ratio at a constant value throughout the reaction or subject it to controlled variation so that it follows a defined variation profile with the passage of time, while being contained within the above-mentioned range of values throughout the reaction.

To optimise the running of the synthesising reaction, it is possible to proceed by intermittently or continuously drawing off at least one constituent of the reaction medium. The constituent(s) drawn off could possibly be returned to the reactor after being fractionated.

In one embodiment of the invention provision may be made to draw off the whole reaction medium intermittently or continuously, and one or more constituents of the medium drawn off may be re-injected into the reactor after fractionation.

The reaction vessel or reactor used for carrying out the method of the invention is advantageously equipped with a temperature control, a pressure control, means for adding reagents and means for drawing off products.

While the synthesising reaction is in process the temperature is advantageously set at from 20 to 100° C., the partial pressure above the reaction medium is advantageously set at from 10 mbar ($10^3$ Pa) to 1000 mbar ($10^5$ Pa) and the reaction medium is advantageously subjected to gentle agitation.

To obtain preparations resulting from sucrose esters of high purity, provision may further be made to carry out additional final fractionating operations, for example through eliminating the residual sugars or fats by extraction by organic solvents or supercritical fluids or through fractionating the monoesters and/or diesters produced by precipitation or chromatographic separation.

The sugar or sugar derivative used in the invention may comprise any compound of the above-mentioned types, particularly compounds of the -ose family.

In a preferred embodiment of the invention the sugar or sugar derivative is chosen from the group formed by fructose, glucose, saccharose, trehalose, ethyl and methyl derivatives of those sugars and compounds of a similar structure such as polyhydric alcohols.

The acyl donor compound is chosen from known fatty acids and may preferably be selected from the group formed by saturated or unsaturated fatty acids with an even or odd number of carbon atoms, straight or branched fatty acids with over 4 carbon atoms, esters of fatty acids, monoglycerides, diglycerides, triglycerides and oils.

The organic solvent used may be any organic compound or any mixture of organic compounds which can totally or partially solubilise the selected sugars or sugar derivatives and acyl donors.

Thus the solvent or solvents may in particular be selected from the following substances: methanol, ethanol, propanol, butanol, acetone, propanone, butanone, pentan-2-one, 1,2-ethanediol, 2,3-butanediol, dioxan, acetonitrile, 2-methylbutan-2-ol, tertiobutanol, 2-methylpropanol and 4-hydroxy-2-methylpentanone, or a mixture of two or more of these solvents.

The enzymatic catalyst used must of course cause and encourage transfer of an acyl group from an acyl donor to a sugar or sugar derivative, and may advantageously comprise a protease or lipase, preferably immobilised on a carrier.

DESCRIPTION OF THE PREFERRED EMBODIMENTS

Taking into account the different features mentioned above, several different embodiments of the invention may be envisaged, particularly according to the nature of the reagents used and the preferred aims to be achieved.

In a first embodiment a synthesising method can thus be envisaged with acyl donor and solvent added during the reaction.

In that case the reactor initially contains the solvent, the total quantity of sugar or sugar derivative (generally from 10 g/l to 200 g/l) necessary to obtain the desired final quantity of sucrose ester, the quantity of acyl donor corresponding to the initial required molar ratio (of dissolved sugar/acyl donor) (generally from 1 g/l to 500 g/l), and the enzyme included in soluble or immobilised form (from 1 g/l to 100 g/l), preferably between 5 g/l and 20 g/l).

While the reaction is proceeding solvent is added, so as to compensate for evaporation losses and maintain a relatively constant quantity of solvent, and acyl donor is also added, in a quantity per unit of time adapted to keep the molar ratio (of dissolved sugar/acyl donor) at the required value.

Thus when it is advantageous to keep this molar ratio constant throughout the reaction the acyl donor is added at a speed equal to its speed of consumption by the reaction; this speed of consumption may be determined by a preliminary kinetic study of the enzyme reaction used. The quantity per unit of time of acyl donor to be added during the reaction is generally from 0.01 to 10 grams of acyl donor per hour per gram of enzyme catalyst present in the reactor.

In a second embodiment of the invention the synthesising method may equally be carried out with the sugar and solvent being added.

In this second case the reactor initially contains the solvent, the total quantity of acyl donor (generally from 1 g/l to 500 g/l) necessary to obtain the desired final quantity of sucrose ester, the quantity of sugar or sugar derivative corresponding to the initial required molar ratio (of dissolved sugar/acyl donor) (generally from 1 g/l to 200 g/l), and the enzyme included in soluble or immobilised form (from 1 g/l to 100 g/l), preferably between 5 g/l and 20 g/l).

While the reaction is proceeding solvent is added, so as to compensate for evaporation losses and maintain a relatively constant quantity of solvent, and sugar or sugar derivative is also added, in a quantity per unit of time adapted to keep the molar ratio (of dissolved sugar/acyl donor) at the required value.

Thus when it is advantageous to keep this molar ratio constant throughout the reaction the sugar or sugar derivative is added at a speed equal to its speed of consumption by the reaction; this speed of consumption may be determined by a preliminary kinetic study of the enzyme reaction used. The quantity per unit of time of sugar or sugar derivative to be added during the reaction is generally from 0.01 to 10 grams of sugar or sugar derivative per hour per gram of enzyme catalyst present in the reactor.

In a third embodiment of the invention the synthesising method may equally be carried out with sugar (or sugar derivative), acyl donor and solvent being added.

In this third case the reactor initially contains the solvent, the sugar at a variable concentration (preferably higher than the solubility of the sugar in the solvent), the quantity of acyl donor corresponding to the initial required molar ratio (of dissolved sugar/acyl donor), and the enzyme included in soluble or immobilised form.

While the reaction is proceeding solvent is added, so as to compensate for evaporation losses, and sugar (or sugar derivative) and acyl donor are also added, in quantities per units of time defined so as to keep the molar ratio of these two constituents at the required value.

When it is advantageous to keep this molar ratio constant throughout the reaction the sugar (or sugar derivative) and acyl donor are added in quantities per units of time respectively equal to their speeds of consumption by the reaction; these speeds of consumption may be determined by a preliminary kinetic study of the enzyme reaction used.

In a fourth embodiment of the invention the continuous synthesising method may alternatively be carried out with sugar (or sugar derivative), acyl donor and/or solvent, and possibly enzymatic catalyst being added and drawn off.

In this fourth case the reactor initially contains the solvent, the sugar at a variable concentration (preferably higher than the solubility of the sugar in the solvent), the quantity of acyl donor corresponding to the initial required molar ratio (of dissolved sugar/acyl donor), and the enzyme included in soluble or immobilised form.

While the reaction is taking place substances are drawn off continuously or intermittently from the reaction medium. The enzyme may be retained inside the reactor when it is in immobilised form.

After separation the solvent and possibly the sugar and/or acyl donor may be recycled to the reactor.

Throughout the reaction solvent is added, so as to compensate for losses through evaporation and drawing off, and sugar (or sugar derivative) and acyl donor are also added, in quantities per unit of time defined so as to keep the molar ratio of these two constituents at the required value.

When it is advantageous to keep this molar ratio constant throughout the reaction the sugar (or sugar derivative) and acyl donor are added in quantities per units of time respectively equal to their speeds of consumption by the reaction and their drawing off rates.

Various practical embodiments of the invention will now be described as non-restrictive examples.

EXAMPLE 1

Production of Fructose Oleate with Intermittent Addition of Fructose 1 litre of 2-methylbutan-2-ol, 25 g of fructose, 106 g of methyl oleate and 5 g of immobilised lipase particles of the type known by the trade name of Novozym are initially placed in a glass reactor. The temperature of the reactor is set to 60° C., the pressure to 200 mbar ($2 \times 10^4$ Pa) and the agitation to 200 rpm (rotations per minute). 25 g of fructose is added after 8 hours' reaction and a further 25 g of fructose after 16 hours' reaction. The molar ratio of fructose/methyl oleate, which is initially set to a value of 0.38, is kept between 0.12 and 5.00 during the reaction.

The following fructose oleate production rates are obtained as the synthesising reaction progresses:

- 45 g/l of monoester and 5 g/l of diester are recorded after 8 hours' reaction. This corresponds to a total conversion of 78% of the fructose and a specific productivity of 1.2 g of sucrose ester per hour per gram of enzyme particles.
- 65 g/l of monoester and 10 g/l of diester are recorded after 16 hours' reaction. This corresponds to a total conversion of 58% of the fructose and a specific productivity of 0.9 g of sucrose ester per hour per gram of enzyme particles.
- 80 g/l of monoester and 10 g/l of diester are recorded after 20 hours' reaction. This corresponds to a total conversion of 46% of the fructose and a specific productivity of 0.9 g of sucrose ester per hour per gram of enzyme particles.

EXAMPLE 2

Production of Fructose Oleate with Continuous Addition of Fructose and Methyl Oleate 500 ml of 2-methylbutan-2-ol, 5 g of fructose, 8.3 g of methyl oleate and 10 g of immobilised lipase particles of the type known by the trade name of Novozym are initially placed in a glass reactor. The temperature of the reactor is set to 60° C., the pressure to 200 mbar ($2 \times 10^4$ Pa) and the agitation rate to 200 rpm (rotations per minute). A solution of 2-methylbutan-2-ol containing 55 mM of fructose and 55 mM of methyl oleate is added during the reaction, at a rate of 1 ml/mn. The molar ratio of fructose/methyl oleate, which is initially set to a value of 1.0, is kept between 0.5 and 1.5 during the reaction.

40 g of fructose oleate monoester is obtained after 20 hours' reaction, without a detectable quantity of diester. This corresponds to a total conversion of 95% of the fructose and 95 of the methyl oleate and a specific productivity of 0.15 g of sucrose ester per hour per gram of enzyme particles.

EXAMPLE 3

Production of Fructose Oleate with Continuous Addition of Methyl Oleate 500 ml of 2-methylbutan-2-ol, 12.5 g of fructose, 8.3 g of methyl oleate and 10 g of immobilised lipase particles of the type known by the trade name of Novozym are initially placed in a glass reactor. The temperature of the reactor is set to 60° C., the pressure to 200 mbar ($2 \times 10^4$ Pa) and the agitation rate to 200 rpm (rotations per minute). A solution of 2-methylbutan-2-ol containing 206 mM of methyl oleate is added during the reaction, at a rate of 0.66 ml/mn. The molar ratio of fructose/methyl oleate, which is initially set to a value of 2.0, is kept between 1.0 and 2.0 during the reaction.

60 g of fructose oleate monoester is obtained after 18 hours' reaction, without a detectable quantity of diester. This corresponds to a total conversion of 95% of the fructose and 95% of the methyl oleate and a specific productivity of 0.3 g of sucrose ester per hour per gram of enzyme particles.

EXAMPLE 4

Production of Trehalose Pelargonate with Continuous Addition of Pelargonic Acid 465 ml of 2-methylbutan-2-ol, 14 g of trehalose, 72 mmol of pelargonic acid and 10 g of immobilised lipase particles of the type known by the trade name of Novozym are initially placed in a glass reactor. The temperature of the reactor is set to 60° C., the pressure to 200 mbar ($2 \times 10^4$ Pa) and the agitation rate to 200 rpm (rotations per minute). A mixture of 32 ml of 2-methylbutan-2-ol and 468 ml of pelargonic acid is added during the reaction and for 12 consecutive hours, at a rate of 0.66 ml/mn. The molar ratio of fructose/pelargonic acid, which is initially set to a value of 0.09, is kept between 0.01 and 0.09 during the reaction.

3 g of trehalose pelargonate monoester and 22 g/l of diester are obtained after 18 hours' reaction. This corresponds to a total conversion of 53% of the trehalose and 3% of the pelargonic acid, and a specific productivity of 0.13 g of sucrose ester per hour per gram of enzyme particles.

2 g of trehalose pelargonate monoester and 25 g/l of diester are obtained after 48 hours' reaction. This corresponds to a total conversion of over 98% of the trehalose and 3% of the pelargonic acid, and a specific productivity of 0.06 g of sucrose ester per hour per gram of enzyme particles.

As shown as an illustration by the various examples described above, the method for enzymatic synthesis of sucrose esters according to the invention has many advantages over similar known methods, and in particular enables the following performance to be obtained, resulting particularly in considerable economic advantages:

final concentrations of sucrose esters which may be up to 90 g/l;

over 95% conversion yields for both the sugar or sugar derivatives and the acyl donor compound;

reaction selectivity of either over 99% of monoesters or over 90% of diesters;

specific productivity of up to 0.7 g of sucrose esters per hour per gram of enzyme particles.

Apart from this performance it should also be noted that the invention gives a well-defined composition for the sucrose esters and thus a higher quality of products.

The absence of parasitic reactions and coloration at the temperatures used (generally about 60° C.) additionally enables purifying operations and effluent production to be minimised, further improving the economic competitiveness of the method according to the invention.

Finally the method is also distinguished from known methods by its very great versatility, enabling it to be applied to a very wide range of sugars (monosaccharides and disaccharides) and acyl donors (fatty acids, fatty acid esters, oils, oil esters) and consequently to produce a very wide range of new sucrose esters.

The invention is not of course restricted to the embodiments described. It can be modified, particularly from the point of view of the make-up of the various components or through substituting technical equivalents, without thereby going outside the scope of protection of the invention.

What is claimed is:

1. A method for the enzymatic synthesis of sucrose esters, which comprises:

introducing in a reactor amounts of an organic solvent, a sugar or sugar derivative, a compound donor of acyl groups, and an enzymatic catalyst to form a reaction medium;

wherein the molar ratio of the sugar or sugar derivative to acyl donor in the reaction medium is controlled in such a way that the molar ratio is from 0.01 to 10.00 throughout the process;

adding additional amounts of the sugar or sugar derivative and/or the acyl donor during the reaction; and finally purifying the resulting sucrose esters at least by separating enzymatic particles and the solvent.

2. The method according to claim 1, further comprising continuously or intermittently adding to the reaction medium additional quantities of at least one of sugar or sugar derivative in solid form or in the form of a liquid solution, solvent, enzymatic catalyst in soluble or immobilized form and acyl donor compound alone or solubilized in the solvent.

3. The method according to claim 1, further comprising intermittently or continuously drawing off at least one constituent of the reaction medium, and returning said at least one drawn off constituent to the reactor after fractionation.

4. The method according to claim 3, further comprising intermittently or continuously drawing off the whole reaction medium, one or more constituents of the medium drawn off being re-injected into the reactor after fractionation.

5. The method according to claim 1, wherein the molar ratio is from 0.02 to 1.00.

6. The method according to claim 1, wherein during the reaction, the temperature is set at from 20 to 100° C., the partial pressure above the reaction medium is set at from 10 mbar to 1000 mbar, and the reaction medium is subjected to agitation.

7. The method according to claim 1, further comprising eliminating residual sugars or fats by extraction with organic solvents or supercritical fluids.

8. The method according to claim 1, further comprising fractionating monoesters and diesters produced by precipitation or chromatographic separation.

9. The method according to claim 1, wherein the sugar or sugar derivative is selected from the group consisting of fructose, glucose, saccharose, trehalose, ethyl and methyl derivatives of these sugars, and polyhydric alcohols.

10. The method according to claim 1, wherein the acyl donor compound is selected from the group consisting of saturated or unsaturated fatty acids with an even or odd number of carbon atoms, straight or branched fatty acids with over 4 carbon atoms, esters of fatty acids, monoglycerides, diglycerides, triglycerides and oils.

11. The method according to claim 1, wherein the organic solvent comprises a solvent selected from the group consisting of methanol, ethanol, propanol, butanol, acetone, propanone, butanone, pentan-2-one, 1,2-ethanediol, 2,3-butanediol, dioxan, acetonitrile, 2-methyl-butan-2-ol, tertiobutanol, 2-methylpropanol and 4-hydroxy-2-methylpentanone, and a mixture of two or more of these solvents.

12. The method according to claim 1, wherein the enzymatic catalyst comprises a protease or lipase.

13. The method according to claim 12, wherein the protease or lipase is immobilized on a carrier.

* * * * *